United States Patent
Colomb et al.

(10) Patent No.: US 9,981,091 B2
(45) Date of Patent: May 29, 2018

(54) DRY POWDER INHALATOR

(71) Applicant: APTAR FRANCE SAS, Le Neubourg (FR)

(72) Inventors: Arnaud Colomb, Verneuil sur Seine (FR); Matthieu Baillet, Bonsecours (FR); Maxime Kirniak, Rouen (FR); Antoine Laut, Wy Dit Joli Village (FR)

(73) Assignee: APTAR FRANCE SAS, Le Neubourg (FR)

(*) Notice: Subject to any disclaimer, the term of this patent is extended or adjusted under 35 U.S.C. 154(b) by 854 days.

(21) Appl. No.: 14/397,342

(22) PCT Filed: May 30, 2013

(86) PCT No.: PCT/FR2013/051213
§ 371 (c)(1),
(2) Date: Oct. 27, 2014

(87) PCT Pub. No.: WO2013/178949
PCT Pub. Date: Dec. 5, 2013

(65) Prior Publication Data
US 2015/0083129 A1 Mar. 26, 2015

(30) Foreign Application Priority Data
May 31, 2012 (FR) .................................... 12 55009

(51) Int. Cl.
*A61M 15/00* (2006.01)
(52) U.S. Cl.
CPC ...... *A61M 15/0051* (2014.02); *A61M 15/004* (2014.02); *A61M 15/007* (2014.02);
(Continued)

(58) Field of Classification Search
CPC .......... A61M 15/0028; A61M 15/0035; A61M 15/0036; A61M 15/004; A61M 15/0045;
(Continued)

(56) References Cited

U.S. PATENT DOCUMENTS

| 5,207,217 A | * | 5/1993 | Cocozza | A61M 15/0045 128/203.15 |
| 5,896,855 A | * | 4/1999 | Hobbs | A61M 15/0028 128/203.12 |

(Continued)

FOREIGN PATENT DOCUMENTS

| FR | 2 909 645 A1 | 6/2008 |
| FR | 2 918 353 A1 | 1/2009 |

(Continued)

OTHER PUBLICATIONS

International Search Report for PCT/FR2013/051213, dated Jul. 26, 2013.
(Continued)

*Primary Examiner* — Kathryn E Ditmer
(74) *Attorney, Agent, or Firm* — Sughrue Mion, PLLC

(57) ABSTRACT

A dry powder inhaler including a main body, a plurality of individual reservoirs, such as blisters, each containing a single dose of powder, and disposed one behind another on a flexible strip, and an opening mechanism provided for opening an individual reservoir each time the device is actuated. The device includes first a displacement mechanism adapted to displace an individual reservoir to face the opening mechanism before and/or after each actuation, and a second displacement mechanism adapted to displace an individual reservoir against the opening mechanism on each actuation. The first displacement mechanism having an indexer wheel provided with a recess that receives an individual reservoir, the recess defined by a bottom wall and an inner side wall of said indexer wheel, and by an outer side (Continued)

wall formed on a separate adjustment element assembled on the indexer wheel.

12 Claims, 2 Drawing Sheets

(52) U.S. Cl.
CPC .... *A61M 15/0008* (2014.02); *A61M 15/0021* (2014.02); *A61M 15/0026* (2014.02); *A61M 15/0036* (2014.02); *A61M 15/0045* (2013.01); *A61M 15/0055* (2014.02); *A61M 15/0058* (2014.02); *A61M 15/0086* (2013.01); *A61M 15/0091* (2013.01); A61M 15/0073 (2014.02); A61M 15/0075 (2014.02); A61M 15/0078 (2014.02); A61M 2202/064 (2013.01)

(58) Field of Classification Search
CPC .......... A61M 15/0051; A61M 15/0086; A61M 15/0091; A61M 15/0093; A61M 15/0096
See application file for complete search history.

(56) References Cited

U.S. PATENT DOCUMENTS

| | | | | |
|---|---|---|---|---|
| 2002/0032409 | A1* | 3/2002 | Ritsche | A61M 15/0045 604/154 |
| 2004/0050385 | A1* | 3/2004 | Bonney | A61M 15/0065 128/203.15 |
| 2004/0099676 | A1* | 5/2004 | Anderson | A61M 15/0045 221/25 |
| 2004/0244794 | A1* | 12/2004 | Richards | A61K 9/0075 128/203.15 |
| 2007/0137645 | A1* | 6/2007 | Eason | A61M 15/0028 128/203.15 |
| 2008/0116220 | A1* | 5/2008 | Pocock | A61M 15/0045 222/80 |
| 2009/0188498 | A1* | 7/2009 | Thoemmes | A61M 15/0045 128/203.21 |
| 2009/0283095 | A1 | 11/2009 | Pocock et al. | |
| 2010/0307492 | A1* | 12/2010 | Fabien | A61M 15/0045 128/203.15 |
| 2010/0307493 | A1* | 12/2010 | Kirniak | A61M 15/0045 128/203.15 |
| 2010/0331765 | A1* | 12/2010 | Sullivan | A61M 11/06 604/24 |

FOREIGN PATENT DOCUMENTS

| | | |
|---|---|---|
| WO | 2006/079750 A1 | 8/2006 |
| WO | 2008/012458 A2 | 1/2008 |
| WO | 2009/007640 A1 | 1/2009 |
| WO | 2009/077700 A2 | 6/2009 |
| WO | 2009/136098 A2 | 11/2009 |

OTHER PUBLICATIONS

International Preliminary Report on Patentability dated Dec. 2, 2014 from the International Searching Authority in counterpart Application No. PCT/FR2013/051213.

* cited by examiner

DRY POWDER INHALATOR

CROSS REFERENCE TO RELATED APPLICATIONS

This application is a National Stage of International Application No. PCT/FR2013/051213, filed May 30, 2013, claiming priority from French Patent Application No. 1255009, filed May 31, 2012, the contents of all of which are incorporated herein by reference in their entirety.

The present invention relates to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally initially loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the preceding dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. Another problem that may occur relates to assembling certain parts, in particular movable parts, that need to withstand large stresses in operation, and for which assembly needs to be particularly reliable so as to avoid any risk of malfunctioning. With the small size of certain parts, it can be complicated to guarantee such reliable assembly. Another problem may occur with devices using perforator means to open an individual reservoir, such as a blister, on each actuation. In order to avoid variations in performance, it is desirable for perforation always to take place at substantially the same location on the blister, if possible at its center. It is thus desirable to be able to predefine the position of each blister accurately relative to the perforator means, so as to guarantee consistency in performance. Document WO 2008/012458 describes a prior-art device.

An object of the present invention is to provide a dry-powder inhaler that does not have the above-mentioned drawbacks.

In particular, an object of the present invention is to provide such a device that is simple and inexpensive to manufacture and to assemble, that can be assembled and used reliably, guaranteeing metering accuracy and reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

The present invention thus provides a dry powder inhaler including a main body, said device including a plurality of individual reservoirs, such as blisters, each containing a single dose of powder, and disposed one behind another on a flexible strip, opening means being provided for opening an individual reservoir each time the device is actuated, said device including first displacement means that are adapted to displace an individual reservoir to face said opening means before and/or after each actuation, and second displacement means that are adapted to displace an individual reservoir against said opening means on each actuation, said first displacement means comprising an indexer wheel provided with at least one recess that receives an individual reservoir, said recess being defined by a bottom wall and an inner side wall of said indexer wheel, and by an outer side wall formed on a separate adjustment element assembled on said indexer wheel.

Advantageously, said indexer wheel includes a plurality of recesses.

Advantageously, said separate adjustment element comprises a central sleeve and an annular outer wall that is connected to said central sleeve via a plurality of spacers, said spacers forming said outer side walls of said recesses of the indexer wheel.

Advantageously, after assembling the separate adjustment element on the indexer wheel, the size of the recesses is substantially equal to, or slightly greater than, the external size of the cavities of the blisters.

Advantageously, the device includes an inhalation trigger system that comprises a deformable air chamber that co-operates with an inhalation piece, and a trigger element that co-operates with said air chamber, such that during inhalation through said inhalation piece, said air chamber is deformed and said trigger element actuates said opening means, such that during inhalation through the inhalation piece, a reservoir is opened by said opening means.

Advantageously, said second displacement means comprise movable support means that are displaceable between a non-dispensing position and a dispensing position, said movable support means being urged towards their dispensing position by resilient means, such as a spring or a spring blade, and being held in their non-dispensing position by blocking means that are released by the user inhaling.

Advantageously, said indexer wheel is rotatably mounted on a pin of said movable support means.

Advantageously, said opening means include a perforator element that is stationary relative to said main body and that is adapted to cut a closure wall of the reservoir in such a manner that the cut portion(s) does/do not obstruct the opening(s) that is/are formed.

Advantageously, the device includes at least one cover element that is mounted to pivot on said main body between a closed position and an open position.

These characteristics and advantages and others of the present invention appear more clearly from the following detailed description, given by way of non-limiting example, and with reference to the accompanying drawing, and in which.

Figure 1:
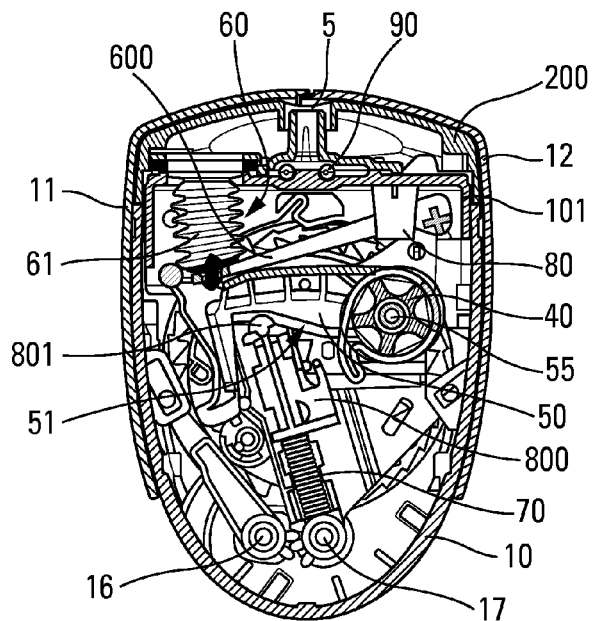
FIGS. 1 to 3 are diagrammatic section views of a dispenser device in an advantageous embodiment of the invention, respectively before opening, after opening but before inhalation, and after inhalation.
Figures 2, 3:
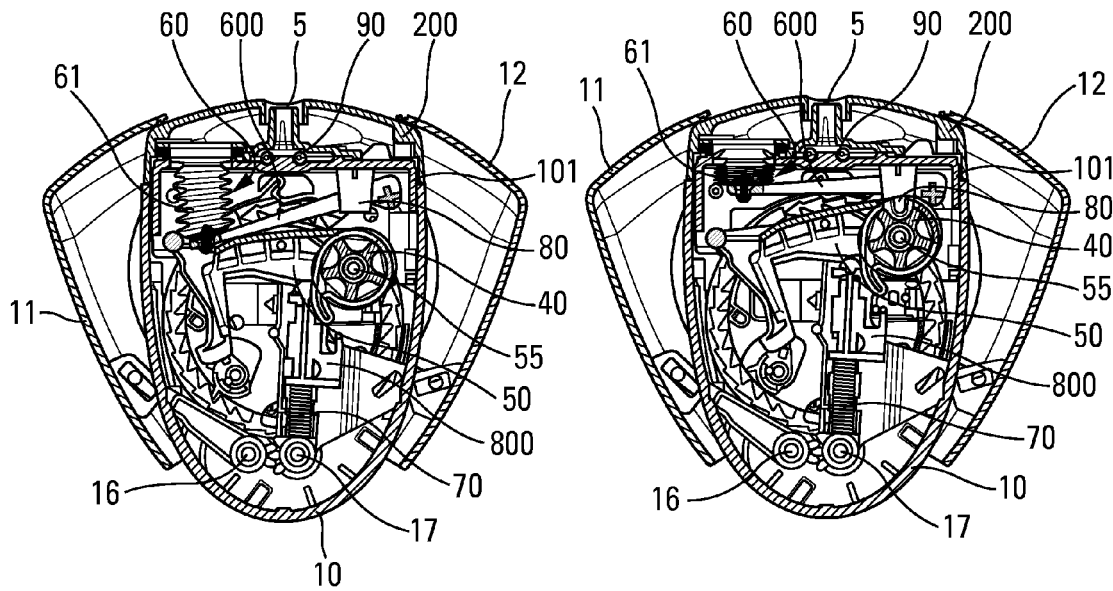

FIGS. 1 to 3 show an advantageous embodiment of a dry-powder inhaler. The inhaler includes a main body 10 on which there can be slidably mounted two cover-forming portions 11, 12 that are adapted to be opened so as to open and prime the device. The main body 10 can be approximately rounded in shape, as shown in the figures, but it could be of any other appropriate shape. An upper body 101 is assembled to the main body 10, and a mouthpiece 200 is assembled on said upper body 101. The mouthpiece 200 defines a dispenser orifice 5 through which the user inhales while the device is being actuated. The dispenser orifice 5 is typically arranged approximately in the center of the mouthpiece 200. The covers 11, 12 can open by pivoting about a common pivot axis, or about two parallel axes by being meshed together. Any other opening means for opening the device can be envisaged. In a variant, the device could include only a single cover instead of two.

Figure 4:
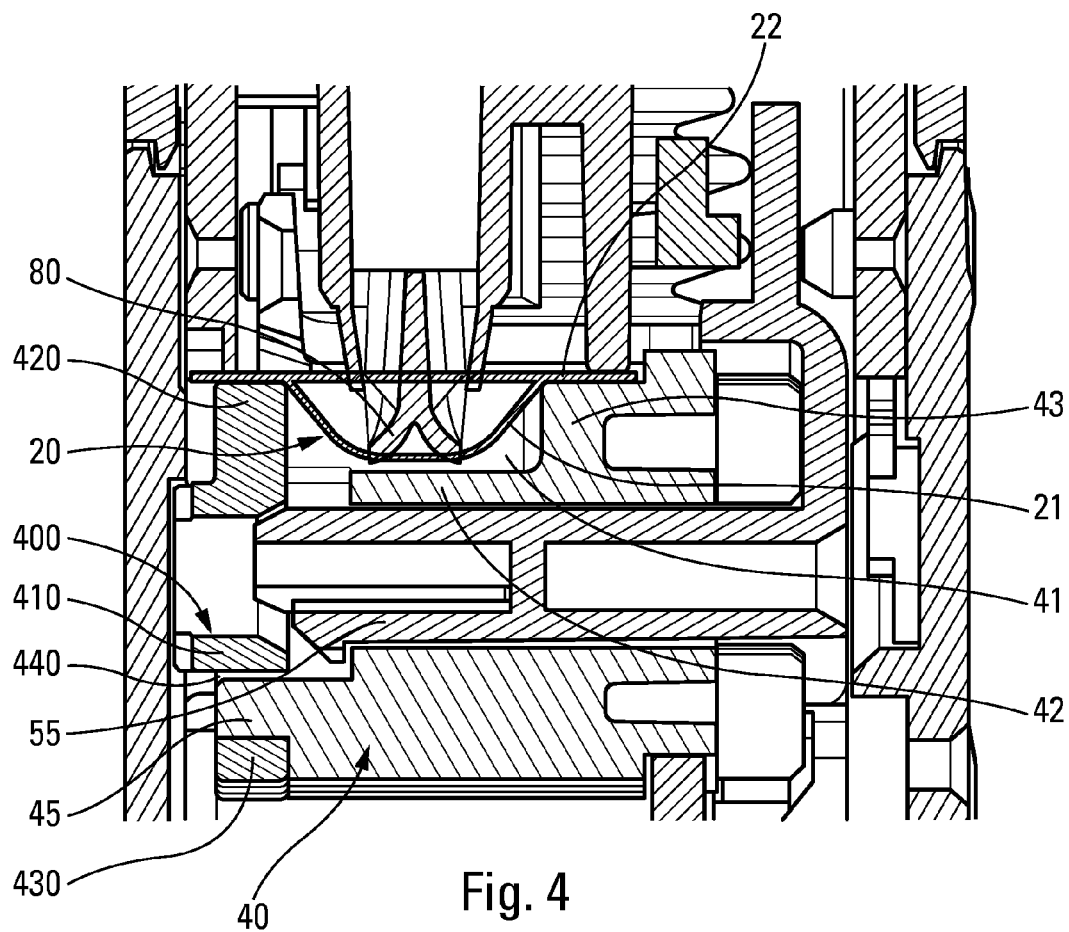
FIG. 4 is a diagrammatic section view of a detail of a portion of the device in FIGS. 1 to 3.

Inside the main body 10 there is provided a strip (not shown for the sake of clarity) of individual reservoirs, also known as blisters, said strip being made in the form of an elongate strip on which the blisters are disposed one behind another, in manner known per se. A blister 20 is shown in FIG. 4. The blister strip is advantageously constituted by a base layer or wall that forms the cavities 21 receiving the doses of powder, and by a closure layer or wall 22 that covers each of said blisters in sealed manner. Before first use, the blister strip can be rolled-up inside the main body 10, preferably in a storage portion, and first strip displacement means 40, in particular rotary means, are provided for progressively unrolling the blister strip and for causing it to advance.

Second displacement means 50, in particular means that are mounted to pivot on the main body 10, are provided for bringing a respective blister into a dispensing position each time the device is actuated. The second displacement means are advantageously mounted to pivot between a non-dispensing position and a dispensing position in which a blister co-operates with said opening means.

The strip portion including the empty blisters is advantageously adapted to be rolled-up at another location of said body 10, preferably a reception portion, as described in greater detail below.

The inhaler includes blister opening means 80 preferably comprising a perforator and/or cutter needle for perforating and/or cutting the closure layer of the blisters. Preferably, the opening means comprise a perforator element 80 that is stationary relative to the main and upper bodies 10, 101, and against which a respective blister 20 is displaced on each actuation by the second displacement means. The blister is thus perforated by said perforator element that penetrates into said blister so as to expel the powder by means of the user inhaling. This position is shown in FIG. 4. Advantageously, the perforator element is adapted to cut a closure wall of the reservoir in such a manner that the cut portion(s) does/do not obstruct the opening(s) that is/are formed. Documents WO 2006/079750 and WO 2009/007640 describe such blister opening means, and they are thus incorporated in the present description by way of reference.

The first displacement means 40 are adapted to cause the blister strip to advance after each inhalation of the user. The second displacement means 50 are adapted to displace the blister to be emptied against said opening means 80 during actuation, before each inhalation. The second displacement means 50 can be urged by a resilient element 70, such as a spring or any other equivalent resilient element, said resilient element being suitable for being prestressed while the device is being opened.

The first displacement means 40 are formed by an indexer wheel that receives and guides the blister strip. The description below is thus made with reference to such an indexer wheel 40. Turning the indexer wheel 40 causes the blister strip to advance. Before each inhalation, a full blister is always in a position facing the opening means 80. The second displacement means 50 include a pivot member, said indexer wheel 40 advantageously being rotatably mounted on a pin 55 of said pivot member 50.

An actuation cycle of the device can be as follows. During opening of the device, the two cover-forming lateral portions 11, 12 are moved away from each other by pivoting about the body so as to open the device and thus spring-load the device. In this position, the indexer wheel 40 cannot be displaced towards the perforator element 80, since the second displacement means 50 are held by appropriate blocking means (not shown for the sake of clarity). Documents WO 2009/077700 and WO 2009/136098 describe such blocking means, and they are thus incorporated in the present description by way of reference. While the user is inhaling through the mouthpiece, the blocking means are unblocked, thereby causing said indexer wheel 40 to move towards the needle, and thereby causing a blister to be opened.

As explained above, it is desirable for the opening means to be actuated by the user inhaling. In order to trigger the opening means by inhalation, an inhalation trigger system 60 is provided that advantageously comprises an air chamber 61 that is deformable under the effect of inhalation, the air chamber being adapted to release the blocking means. The air chamber 61 may advantageously be made in the form of a bellows. Inhalation by the user causes said deformable air-chamber to deform, thereby releasing said blocking means and enabling the second displacement means to be displaced, and therefore enabling a respective blister to be displaced towards its opening position. The blister is therefore opened only on inhalation, such that it is emptied simultaneously. Thus, there is no risk of any of the dose being lost between opening the blister and emptying it.

The inhaler further includes a dispersion chamber 90 for receiving the dose of powder after a respective blister has been opened. The dispersion chamber is advantageously provided with at least one and preferably more beads that are displaced inside said chamber 90 during inhalation, in particular so as to improve dispensing of the air and powder mixture after a blister has been opened, in order to increase the effectiveness of the device.

It can be advantageous for the opening means, in particular for the perforator element, to be connected directly to said dispersion chamber, e.g. via a channel leading to said chamber 90.

After inhalation, when the user closes the device, all of the components return to their initial, rest positions. The device is thus ready for a new utilization cycle.

In an advantageous aspect of the inhaler, the blisters are formed on a flexible elongate strip that, initially, is mainly stored in the form of a roll in a storage housing inside the main body 10 of the device. Advantageously, the rolled-up blister strip is held by inner walls of said storage housing without its rear end (rear in the advancement direction of the blister strip) being fastened relative to said main body 10, thereby enabling the blister-strip roll to be assembled more easily inside the device. The blister strip is displaced by means of the indexer wheel 40 that advantageously presents at least one and preferably more recesses. Thus, when the indexer wheel 40 turns, it causes the blister strip to advance. Naturally, in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of sprocket wheels co-operating with said holes.

After opening one or more blisters, the blister-strip portion with the empty blisters must be suitable for being stored in easy and compact manner in the device, while avoiding any risk of blockage. Advantageously, the used blister strip is rolled-up automatically, once again forming a roll.

In still another aspect of the inhaler, a dose counter or indicator device (not shown for the sake of clarity) may also be provided. The device may include numbers or symbols that are marked directly on the blister strip, and that are visible through an appropriate window in the main body 10 of the device. In a variant, it is possible to envisage using a counter with one or more rotary disks or rings including numbers or symbols. Documents WO 2008/012458 and WO 2011/154659 describe such counters, and they are thus incorporated in the present description by way of reference. An object of the invention is to avoid counting doses that have not been dispensed, e.g. in the event of a manipulation error, or of an incomplete manipulation of the device. It is thus desirable that the counter or indicator is actuated only once the user has inhaled, since it is this inhalation that makes it possible for the blister to open and the dose contained therein to be dispensed. Advantageously, the counter is thus actuated after inhalation, when the user closes the device.

The movable cover element 12 is secured to a cocking member 800 that can slide in an appropriate housing. The cocking member 800 thus advantageously pivots relative to said body 10 together with the cover element 12. The cocking member 800 may be moved against a spring 70, advantageously a coil spring, that is arranged in said housing. The cocking member 800 is thus connected at one end to said spring 70, and at the other end it co-operates with the second displacement means, in particular with a pivot member 50 that is mounted to pivot on the body 10, and on which the indexer wheel 40 is fastened is rotary manner.

When the movable cover element 12 is opened, the cocking member 800 is displaced in its housing, compressing the spring 70. The pivot member 50 of the second displacement means is itself prevented from moving by the above-mentioned blocking means that are released only at the moment of inhalation. Thus, in the absence of any inhalation in the open position, closing the cover elements 11, 12 would merely cause the cocking member 800 to return to its rest position and the spring 70 to decompress.

Thus, by opening the inhaler, the user primes the system. If the user does not inhale and closes the inhaler, said inhaler merely returns to its start position without displacing the blister strip or the blocking means. There is thus no risk of a blister (and thus an active dose of substance) being lost by accidental or incomplete actuation in which the user does not inhale between opening and closing. Opening the blister, emptying it, dispensing the powder into the lungs of the user, displacing the blister strip to bring a new full blister to face the opening means, and counting the dose are thus possible only if the user inhales.

The blocking means that block the second displacement means and in particular the pivot member that co-operates with the cocking member, are connected to the deformable air chamber 61 that is sensitive to the user inhaling, via a trigger element 600, so that while the user is inhaling, said deformable air chamber deforms, causing the trigger element 600 to pivot and causing said blocking means to be released. This enables said second displacement means to be displaced towards their dispensing position under the effect of the force exerted by the compressed spring 70 on the cocking member 800 that pushes against the pivot member 50. Such displacement causes a full blister to be opened and a dose to be dispensed.

A cam surface 51 is formed on said movable support means 50, on which the cocking member 800 slides. The cocking member 800 is thus adapted to compress the spring 70 when the cover element 12 is open, and to decompress said spring 70 when said cover element 12 is closed.

Advantageously, in its portion in contact with the cam surface 51, the cocking member 800 includes a rounded portion 801 for facilitating sliding of the cocking member 800 on said cam surface 51.

In this embodiment, the movable support means are made in the form of a member 50 that is pivotally mounted on the body 10 about a pivot axis. Since the above-mentioned cam surface 51 is formed on said pivot member 50, when the spring 70 is loaded while the movable cap element 12 is opening, said pivot member 50 is urged towards its dispensing position by said cocking member 800 and the spring 70 is compressed.

The cam surface 51 may include at least two portions of different slopes that are advantageously separated by a vertex. Starting from the closed position of the movable cover element, a loader portion on which the cocking member 800 slides, enables the spring 70 to be compressed, as described above. When the spring is loaded, i.e. compressed, the cam surface 51 may provide a second different slope portion with which the cocking member 800 co-operates when the device is in its open position. The cocking member 800 preferably exerts a force that is substantially perpendicular on the second cam surface portion. In this way, the loaded position is stable. In a variant, the second slope portion forms an abutment notch in which the cocking member 800 comes to be positioned in the open position.

After inhalation, i.e. in the dispensing position, the blocking means have been released, and the movable support means 50 have been displaced upwards by the compressed spring 70.

Advantageously, the two movable cover elements 11, 12 mesh together via appropriate gearing so as to guarantee symmetrical opening and closing of said two movable cover elements. They can mesh together in the proximity of their pivot axes 16, 17.

The indexer wheel 40 includes at least one (and advantageously five) recesses 41 for receiving a cavity 21 of a respective blister 20.

The recesses 41 are advantageously defined by a bottom wall 42 and an inner side wall 43 that form an integral part of the indexer wheel 40.

In the invention, an outer side wall 420 of the recesses 41 is formed by a separate adjustment element 400.

Thus, during assembly, the blister strip is assembled on the indexer wheel 40, disposing at least one cavity 21 of a blister 20 in a recess 41, with the closure wall 22 of the blister 20 extending outside said recess 41. The separate adjustment element 400 is thus assembled on the indexer wheel 40, such that the outer side wall 420 of the recess defines a size of recess 41 that is substantially equal to, or slightly greater than, the external size of the cavity 21 of the blister. In this way, all of the cavities are positioned substantially in the same position on the indexer wheel 40, with reproducible perforation thus being achieved substantially at the same location on the blister 20 on each actuation. Furthermore, there is no risk of the blister strip being offset relative to the indexer wheel, since the separate adjustment element positions the cavity 21 of the blister accurately in the recess 41.

Figure 5:
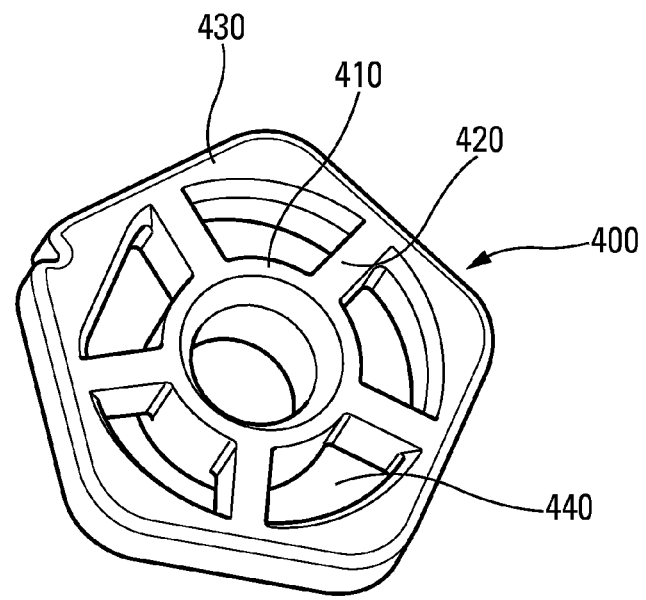
FIG. 5 is a diagrammatic perspective view of the separate adjustment element.

Advantageously, the separate adjustment element 400 include a hollow central sleeve 410 that can receive the pin 55 of the pivot member 50. An annular outer wall 430, that is cylindrical or of polygonal outer shape as can be seen in FIG. 5, is connected to said hollow central sleeve 410 via spacers 420 which, after assembling the separate adjustment element 400 on the indexer wheel 40, form the outer side walls of the recesses 41. One or more openings 440, formed between the central sleeve 410, the annular outer wall 430, and the spacers 420, can receive projections 45 of the indexer wheel, so as to ensure that the separate adjustment element 400 is assembled on the indexer wheel 40.

The present invention therefore makes it possible to provide a dry-powder inhaler that provides the following features:
- a plurality of individual doses of powder stored in individual sealed blisters, e.g. 30 or 60 doses stored on a rolled-up strip;
- the powder is released by perforation that is achieved by the user inhaling, the blister being perforated by means of an inhalation detector system that is coupled to a prestressed release system;
- appropriately-shaped drive means that are engaged with blisters so as to displace the blister strip after each inhalation, and bring a new full blister into a position in which it is to be opened by appropriate opening means;
- means for avoiding doses being lost in the event of the inhaler being opened, but in the absence of any inhalation; and
- a dose indicator adapted to count the doses only in the event of inhalation.

Other features are also provided by the device of the invention as described above.

It should be observed that the various features, even if they are shown as being provided simultaneously on the inhaler, could be implemented separately. In particular, the inhalation trigger mechanism could be used regardless of the type of reservoir opening means, regardless of the use of a dose indicator, regardless of the way in which the individual blisters are arranged relative to one another, etc. The cocking means and the inhalation trigger system could be made in some other way. The same applies for other component parts of the device.

Various modifications are also possible for the skilled person without departing from the scope of the present invention as defined in the accompanying claims. In particular, the various characteristics and functions of the device described with reference to the drawings can be combined together in any appropriate manner.

The invention claimed is:

1. A dry powder inhaler device including a main body, said device comprising:
   a plurality of individual reservoirs, each reservoir containing a single dose of powder and disposed one behind another on a flexible strip;
   opening means for opening an individual reservoir each time the device is actuated;
   first displacement means adapted to displace an individual reservoir to face said opening means before and/or after each actuation; and
   second displacement means adapted to displace an individual reservoir against said opening means on each actuation;
   said first displacement means comprising an indexer wheel provided with a recess that receives an individual reservoir, said recess is defined by a bottom wall and an inner side wall of said indexer wheel and by an outer side wall formed on a separate adjustment element assembled on said indexer wheel.

2. The inhaler according to claim 1, wherein said indexer wheel includes a plurality of recesses.

3. The inhaler according to claim 2, wherein said separate adjustment element comprises a central sleeve and an annular outer wall that is connected to said central sleeve via a plurality of spacers, said spacers forming said outer side walls of said recesses of the indexer wheel.

4. The inhaler according to claim 2, wherein, after assembling the separate adjustment element on the indexer wheel, the size of the recesses is substantially equal to, or slightly greater than, the external size of cavities of the individual reservoirs.

5. The inhaler according to claim 1, including an inhalation trigger system that comprises a deformable air chamber that co-operates with an inhalation piece, and a trigger element that co-operates with said air chamber, such that during inhalation through said inhalation piece, said air chamber is deformed and said trigger element actuates said opening means, such that during inhalation through the inhalation piece, a reservoir is opened by said opening means.

6. The inhaler according to claim 1, wherein said second displacement means comprise movable support means that are displaceable between a non-dispensing position and a dispensing position, said movable support means being urged towards their dispensing position by resilient means and being held in their non-dispensing position by blocking means that are released by the user inhaling.

7. The inhaler according to claim 6, wherein said indexer wheel is rotatably mounted on a pin of said movable support means.

8. The inhaler according to claim 6, wherein the resilient means comprises a spring or a spring blade.

9. The inhaler according to claim 1, wherein said opening means include a perforator element that is stationary relative to said main body and that is adapted to cut a closure wall of each one of the plurality of individual reservoirs in turn in such a manner that the cut portion does not obstruct the opening that is formed.

10. The inhaler according to claim 1, including at least one cover element that is mounted to pivot on said main body between a closed position and an open position.

11. The inhaler according to claim 1, wherein the plurality of individual reservoirs are blisters.

12. The inhaler according to claim 11, wherein, after assembling the separate adjustment element on the indexer wheel, the size of the recess is substantially equal to, or slightly greater than, the external size of cavities of the blisters.

\* \* \* \* \*